United States Patent [19]

Millauro

[11] Patent Number: 5,099,525

[45] Date of Patent: Mar. 31, 1992

[54] FACE PROTECTING MASK INTENDED TO BE USED IN GENERAL MEDICINE AND MORE PARTICULARLY IN SURGERY

[76] Inventor: Carlo Millauro, Via A. Richelmy, 38-00165 Rome, Italy

[21] Appl. No.: 312,659

[22] Filed: Feb. 21, 1989

[30] Foreign Application Priority Data

Nov. 9, 1988 [IT] Italy .................. 48541 A/88

[51] Int. Cl.$^5$ ............................................. A61F 9/00
[52] U.S. Cl. ................................................ 2/9; 2/206;
128/206.19; 128/206.21; 128/857
[58] Field of Search ............... 2/4, 5, 9, 10, 69.5,
2/70, 84, 202.13, 204.15, 206, 435, 436;
128/205.24, 206.12, 206.17, 206.19, 206.21, 857

[56] References Cited

U.S. PATENT DOCUMENTS

| | | | |
|---|---|---|---|
| 437,995 | 10/1890 | Jensen | 2/202 X |
| 1,354,433 | 9/1920 | De-Felice | 2/435 |
| 1,356,542 | 10/1920 | McNeil | 2/10 |
| 1,562,350 | 11/1925 | Luckey | 2/435 X |
| 1,679,105 | 7/1928 | Tully et al. | 2/436 |
| 1,871,534 | 8/1932 | Kimball | 2/436 |
| 1,989,876 | 2/1935 | Meyrowitz | 2/436 X |
| 2,189,892 | 2/1940 | Fox | 2/4 |
| 2,280,055 | 4/1942 | Andersen | 2/435 |
| 2,314,889 | 3/1943 | Manson et al. | 2/9 X |
| 2,435,653 | 2/1948 | Maurer | 2/436 X |
| 2,462,258 | 2/1949 | Dannenberg | 2/10 X |
| 2,526,737 | 10/1950 | Farina | 2/436 |
| 2,589,575 | 3/1952 | Richardsen et al. | 2/436 X |
| 2,612,639 | 10/1952 | Christensen et al. | 2/435 |
| 2,612,640 | 10/1952 | Palmes | 2/436 |
| 2,665,686 | 1/1954 | Wood et al. | 2/436 |
| 3,561,010 | 2/1971 | Little | 2/173 |
| 3,885,558 | 5/1975 | Belkin | 2/173 X |
| 4,011,595 | 3/1977 | Shields | 2/436 |
| 4,126,131 | 11/1978 | Davis et al. | 2/436 X |
| 4,141,086 | 2/1979 | Jackson | 2/436 |
| 4,150,443 | 4/1979 | McNeilly | 2/436 |
| 4,296,746 | 10/1981 | Mason, Jr. et al. | 128/206.12 |
| 4,382,303 | 5/1983 | Lunt | 2/114 |
| 4,387,471 | 6/1983 | Hsu et al. | 2/10 |
| 4,411,023 | 10/1983 | Pinson | 2/205 X |
| 4,622,699 | 11/1986 | Spriggs | 2/DIG. 7 X |
| 4,671,775 | 6/1987 | Hill | 2/202 |
| 4,701,965 | 10/1987 | Landis | 128/857 |
| 4,764,990 | 8/1988 | Markert | 2/436 X |
| 4,768,235 | 9/1988 | Webster | 2/205 |
| 4,805,639 | 2/1989 | Dial et al. | 128/857 |
| 4,845,779 | 7/1989 | Wheeler et al. | 2/84 |
| 4,966,140 | 10/1990 | Herzberg | 2/206 X |

FOREIGN PATENT DOCUMENTS

| | | | |
|---|---|---|---|
| 0150848 | 9/1981 | Fed. Rep. of Germany | 2/436 |
| 873113 | 6/1942 | France | 128/206.24 |
| 0935100 | 6/1982 | U.S.S.R. | 2/436 |
| 2105177 | 3/1983 | United Kingdom | 2/202 |
| 2171814 | 9/1986 | United Kingdom | 2/436 |

Primary Examiner—Werner H. Schroeder
Assistant Examiner—Jeanette E. Chapman
Attorney, Agent, or Firm—Lipton & Famiglio

[57] ABSTRACT

This face protecting mask is intended to be used in general medicine and more particularly in surgery. In its preferred embodiment, the mask has a shell or top portion provided with an elastic band fitted in the rear portion of the trim thereof; a downward front shield provided with an eye-window covered by a strip of a transparent flexible material and a mouth-opening placed below the eye-window and closed by a wad of filtering material; two side protection flaps connected to the front shield; two pairs of string for tying the mask; means for preventing mist from forming on the transparent window; and means for keeping the front shield away from the operator's face.

12 Claims, 2 Drawing Sheets

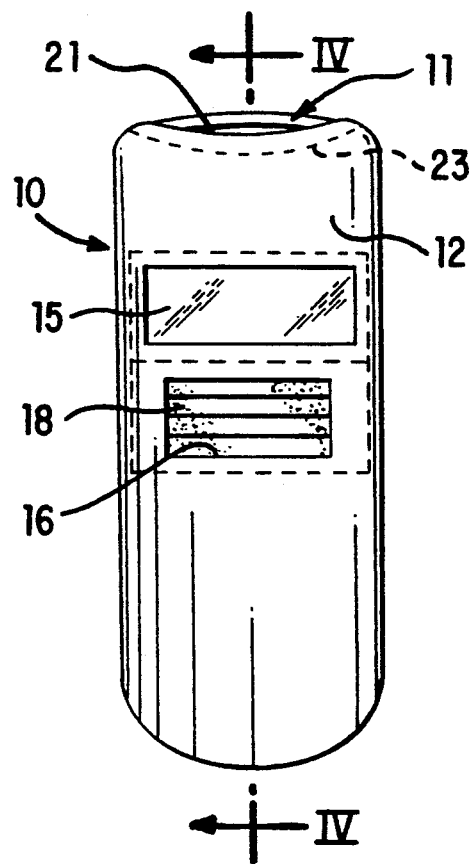
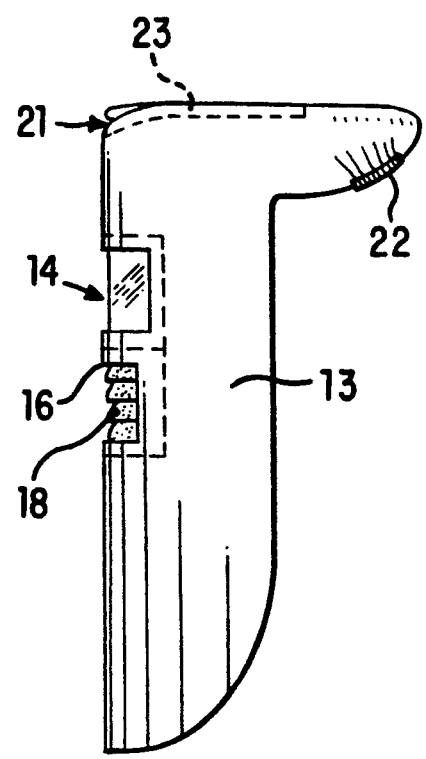
FIG. 1  FIG. 2
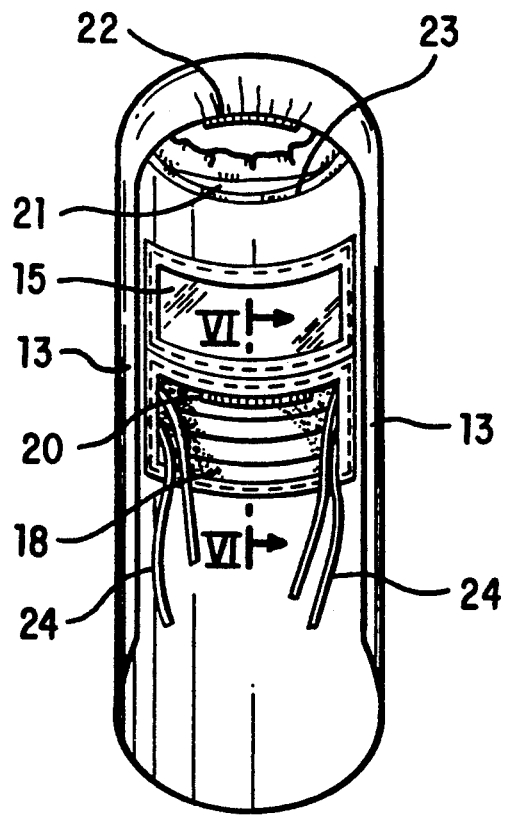
FIG. 3

FACE PROTECTING MASK INTENDED TO BE USED IN GENERAL MEDICINE AND MORE PARTICULARLY IN SURGERY

BACKGROUND OF THE INVENTION

This invention relates to medical and surgical protective wear, and in particular to medical and surgical masks.

In the medical field, the present hygienic and sanitary situation made the use of protective elements even more necessary to the operators.

Thus, particularly in the surgical field, the protection offered by the masks used at present that cover only the mouth, the lower portion of the nose and the surrounding areas has become insufficient.

Accordingly, new protection masks should be provided offering a nearly total protection of the operator's head and neck without causing any secondary drawbacks due to the integral structure thereof.

SUMMARY OF THE INVENTION

This invention refers to a face protecting mask intended to be used in general medicine and more particularly in surgery. Its preferred embodiment has a shell or top portion provided with an elastic band fitted in the rear portion of the trim thereof; a downward front shield provided with an eye-window covered by a strip of a transparent flexible material and a mouth-opening placed below the eye-window and closed by a wad of a filtering material; two side protection flaps connected to the front shield; two pairs of strings for tying the mask; means for preventing mist from forming on the transparent window; and means for keeping the front shield away from the operator's face.

Accordingly, it is an object of the invention to provide an integrally formed mask offering a complete protection of the upper, front and side portions of the head, including the ears and the neck, which can be comfortably used in directly or indirectly highly heated rooms, such as operating rooms.

BRIEF DESCRIPTION OF THE DRAWINGS

FIG. 1 is a front view of the mask.
FIG. 2 is a side view.
FIG. 3 is a rear perspective view.

DETAILED DESCRIPTION OF THE PREFERRED EMBODIMENT

Figure 4:
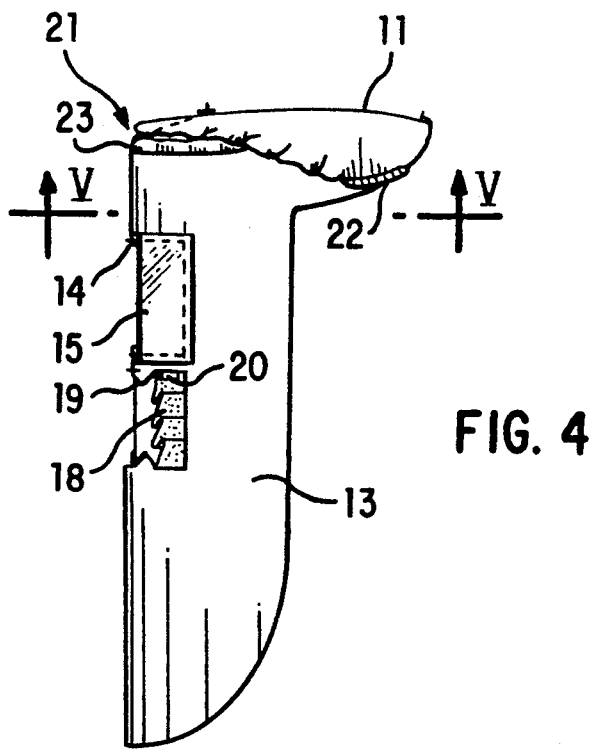
FIG. 4 is a sectional view taken on line 4—4 of FIG. 3.
Figure 5:
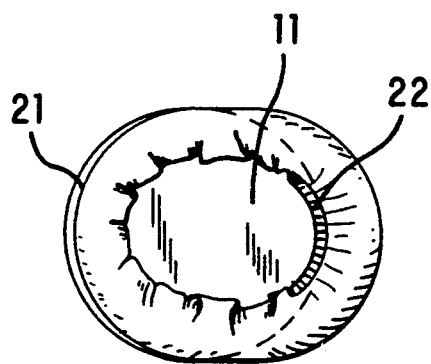
FIG. 5 is a sectional view taken on line 5—5 of FIG. 4.

As shown in the figures, the mask referred to by reference 10 substantially comprises a top shell 11 and a front shield 12 downwardly extending therefrom having two side flaps 13 for protecting the sides of the operator's head, the upper portion of flaps 13 extending rearwardly and joining to shell 11, thus forming an integral piece.

At the level of the operator's eyes, shield 12 has a rectangular opening 14 protected by a band 15 made of a flexible transparent material, thus forming a "window" allowing the operator to see.

A similar rectangular opening 16 is formed immediately below window 14 at the level of the operator's mouth, which opening 16 is closed by an air filter or "wad" 18 of a material filtering the air breathed by the operator.

Figure 6:
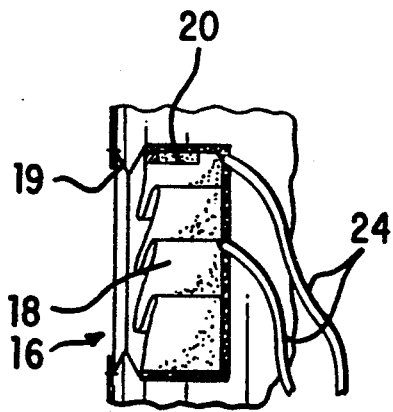
FIG. 6 is an enlarged view of a detail of FIG. 4.
Figure 7:
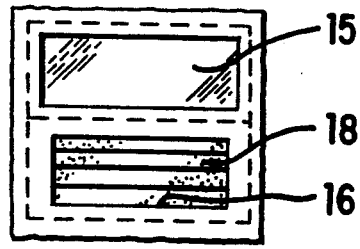
FIG. 7 is an enlarged view of a detail of FIG. 1.

It should be noted that the whole edge of filtering wad 18 is connected to the edge of opening 16 by a "folding" frame 19, as clearly shown in FIGS. 4 and 6. Furthermore, a listel of a soft foamed material referred to by 20 is attached to the upper edge of wad 18 and is adapted to be in contact with the wear's face.

As better shown in FIGS. 1,2, and 3, the central portion of the upper edge of front shield 12 is not joined to the corresponding length, of the, upper edge of shell 11, which is bent, thus forming at the junction of the shield and shell, a small opening or slot 21 in this area.

Furthermore, a piece of elastic band referred to by reference 22 is fitted in the rear portion of top shell 11, the elastic band allowing the shell to tighten on the operator's head.

Finally, a substantially semicircular strip 23 of a semi-rigid material is joined to the upper edge of front shield 12 at the junction thereof with the top of shell 11.

Masks 10 is completed by two pairs of strings 24, one at each side, attached at the sides of filter 18, which closes opening 16.

It should be noted that the mask having the above-described and illustrated configuration offers a nearly complete protection to the operator's face, head and neck, assuring a maximum hygiene both to the patient and to the operator.

The particular and unique comfort offered by the mask of the invention is due to the simultaneous presence of listel 20 placed at the top of filter 18 and opening 21 on one hand and of strip 23 on the other hand.

Listel 20, which is in contact with and rests on the operator3 s nose and cheeks, prevents the vapor contained in the expelled air from condensing on transparent window 15, while the opening helps the air circulation in the upper portion of the mask and is essential in preventing also the vapors due to perspiration from condensing on window 15.

Semicircular strip 23 keeps front shield 12 away from the operator's face and this is particularly convenient in case the operator wears spectacles.

The further advantage due to folding frame 19 should also be noted, which frame allows any movement of filter 18 without causing any movements of transparent window 15 that could be uncomfortable.

The materials used will preferably be viscose, not woven tissue containing polypropylene for shell 11, shield 12 and flaps 13 and a similar material having a higher density for filter 18.

Finally, transparent band 15 of window 14 will preferably be made of polyester.

Listel 20 and strip 23 will preferably be provided with a self-adhesive material allowing the same to be easily place in position on the mask.

There are various changes and modifications that may be made to the present invention, as would be apparent to those skilled in the art. However, any of those changes and modifications are included in the teaching of this disclosure, and it is intended that this invention be limited only by the scope of the claims appended hereto.

What is claimed is:
1. A mask for protecting an operator's head and intended for use in medicine and surgery, comprising:
    (a) a top shell;

(b) a front shield attached to the top shell, having:
  (i) an eyes opening therethrough covered by a window of transparent, flexible material; and
  (ii) a mouth opening placed below the eye window closed by an air filter attached to the front shield;
(c) means for preventing mist from forming on the window;
(d) means for helping air circulate within the mask with includes a junction of said shield with said shell having a vent opening between said shield and said shell; and
(e) means for keeping the front shield away from the operator's face.

2. The protection mask according to claim 1, wherein said means for preventing mist from forming on said window comprises a listel of a soft material resting on the operator's nose and cheeks, preventing vapor contained in expelled air from moving upwards to said transparent window and condensing thereon.

3. The protection mask according to claim 1, wherein said means for keeping said shield away from the operator's face comprises a semicircular strip of a semirigid material connected to the upper edge of said front shield.

4. The protection mask according to claim 1, wherein said shell, shield and side flaps are made of a viscose, not woven tissue containing polypropylene.

5. The protection mask according to claim 4, wherein said filter is made of a viscose, not woven tissue containing polypropylene, having a higher density than the tissue of which said shell, shield, and side flaps are made.

6. The protection mask according to claim 1, wherein said window is made of polyester.

7. A mask for protecting an operator's head and intended for use in medicine and surgery, comprising:
(a) a top shell;
(b) a front shield attached to the top shell, having:
  (i) an eyes opening therethrough covered by a window of transparent, flexible material; and
  (ii) a mouth opening placed below the eye window closed by an air filter connected to the edge of said opening by a folding frame, and attached to the front shield;
(c) means for preventing mist from forming on the window;
(d) means for helping air circulate within the mask; and
(e) means for keeping the front shield away from the operator's face.

8. The protecting mask according to claim 7 wherein said means for preventing mist from forming on said window comprises a listel of a soft material resting on the operator's nose and cheeks, preventing vapor contained in expelled air from moving upwards to said transparent window and condensing thereon.

9. The protecting mask according to claim 7, wherein said means for keeping said shield away from the operator's face comprises a semiciruclar strip of a semirigid material connected to the upper edge of said front shield.

10. The protection mask according to claim 7, wherein sand shell, shield and side flaps are made of a viscose, not woven tissue containing polypropylene.

11. The protecting mask according to claim 10, wherein said filter is made of a viscose, not woven tissue containing polypropylene, having a higher density than the tissue of which said shell, shield, and side flaps are made.

12. The protecting mask according to claim 7, wherein said window is made of polyester.

* * * * *